US010227697B2

(12) United States Patent
Robb et al.

(10) Patent No.: US 10,227,697 B2
(45) Date of Patent: *Mar. 12, 2019

(54) SURFACE TREATMENT PROCESS FOR IMPLANTS MADE OF TITANIUM ALLOY

(75) Inventors: T. Tait Robb, Stewart, FL (US); Bruce Berckmans, III, Palm Beach Gardens, FL (US); Ross W. Towse, Palm City, FL (US); Robert L. Mayfield, Jupiter, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 798 days.

This patent is subject to a terminal disclaimer.

(21) Appl. No.: 13/558,037

(22) Filed: Jul. 25, 2012

(65) Prior Publication Data

US 2012/0288828 A1 Nov. 15, 2012

Related U.S. Application Data

(63) Continuation of application No. 10/843,916, filed on May 12, 2004, now Pat. No. 8,251,700.
(Continued)

(51) Int. Cl.
*A61C 8/00* (2006.01)
*C23F 1/26* (2006.01)
*A61L 27/06* (2006.01)
*A61L 27/50* (2006.01)
*A61F 2/30* (2006.01)

(52) U.S. Cl.
CPC ............. *C23F 1/26* (2013.01); *A61L 27/06* (2013.01); *A61L 27/50* (2013.01); *A61C 2008/0046* (2013.01); *A61F 2/3094* (2013.01); *A61F 2/30767* (2013.01); *A61F 2/30771* (2013.01); *A61F 2002/30925* (2013.01);
(Continued)

(58) Field of Classification Search
CPC ............................................. A61C 2008/0046
USPC ..... 433/173, 201.1; 623/16.11, 22.36, 23.36, 623/23.55
See application file for complete search history.

(56) References Cited

U.S. PATENT DOCUMENTS 3,022,783 A 2/1962 Tucker, Jr.
3,605,123 A 9/1971 Hahn
(Continued)

FOREIGN PATENT DOCUMENTS

AT 328 067 5/1975
CA 926552 5/1973
(Continued)

OTHER PUBLICATIONS

A histomorphometric and removal torque study of screw-shaped titanium implants with three different surface topographies (Ref. D33), dated prior to May 2004.
(Continued)

*Primary Examiner* — Ralph Lewis
(74) *Attorney, Agent, or Firm* — Schwegman Lundberg & Woessner, P.A.

(57) ABSTRACT

A titanium 6 Al/4V alloy is provided with a surface topography that is similar to the Osseotite® surface produced on commercially pure titanium. Native oxide is removed from the Ti 6Al/4V alloy, followed by contacting the metal at ambient temperature with an aqueous hydrochloric acid solution containing a relatively small amount of hydrofluoric acid.

11 Claims, 13 Drawing Sheets

Related U.S. Application Data

(60) Provisional application No. 60/471,463, filed on May 16, 2003.

(52) U.S. Cl.
CPC . *A61F 2310/00023* (2013.01); *A61L 2400/18* (2013.01); *Y10T 29/49567* (2015.01)

(56) References Cited

U.S. PATENT DOCUMENTS

| | | | |
|---|---|---|---|
| 3,767,437 A | 10/1973 | Cruz, Jr. | |
| 3,790,507 A | 2/1974 | Hodosh | |
| 3,855,638 A | 12/1974 | Pilliar | |
| 3,919,723 A | 11/1975 | Heimke et al. | |
| 3,986,212 A | 10/1976 | Sauer | |
| 3,987,499 A | 10/1976 | Scharbach et al. | |
| 4,011,602 A | 3/1977 | Rybicki et al. | |
| 4,051,598 A | 10/1977 | Sneer | |
| 4,145,764 A | 3/1979 | Suzuki et al. | |
| 4,146,936 A | 4/1979 | Aoyage et al. | |
| 4,180,910 A | 1/1980 | Straumann et al. | |
| 4,195,409 A | 4/1980 | Child | |
| 4,199,864 A | 4/1980 | Ashman | |
| 4,223,412 A | 9/1980 | Aoyagi et al. | |
| 4,261,350 A | 4/1981 | Branemark et al. | |
| 4,330,891 A | 5/1982 | Branemark et al. | |
| 4,336,618 A | 6/1982 | Branemark et al. | |
| 4,366,183 A | 12/1982 | Ghommidh et al. | |
| 4,406,761 A | 9/1983 | Shimogori et al. | |
| 4,530,116 A | 7/1985 | Frey | |
| 4,547,157 A | 10/1985 | Driskell | |
| 4,547,327 A | 10/1985 | Bruins et al. | |
| 4,608,052 A | 8/1986 | Van Kampen et al. | |
| 4,629,464 A | 12/1986 | Takata et al. | |
| 4,654,314 A | 3/1987 | Takagi et al. | |
| 4,687,675 A | 8/1987 | Nakano et al. | |
| 4,693,986 A | 9/1987 | Vit et al. | |
| 4,702,930 A | 10/1987 | Heide et al. | |
| 4,704,126 A | 11/1987 | Haswell et al. | |
| 4,722,688 A | 2/1988 | Lonca | |
| 4,746,532 A | 5/1988 | Suzuki et al. | |
| 4,818,559 A * | 4/1989 | Hama et al. | 427/2.27 |
| 4,826,434 A | 5/1989 | Krueger | |
| 4,839,215 A | 6/1989 | Starling | |
| 4,861,733 A | 8/1989 | White | |
| 4,865,603 A | 9/1989 | Noiles | |
| 4,871,578 A | 10/1989 | Adam et al. | |
| 4,874,434 A | 10/1989 | Riggs, Jr. | |
| 4,878,914 A | 11/1989 | Miwa et al. | |
| 4,882,196 A | 11/1989 | Shimamune et al. | |
| 4,908,030 A | 3/1990 | Linkow et al. | |
| 4,911,953 A | 3/1990 | Hosonuma et al. | |
| 4,919,751 A | 4/1990 | Sumita et al. | |
| 4,932,868 A | 6/1990 | Linkow et al. | |
| 4,938,938 A | 7/1990 | Ewers et al. | |
| 4,944,754 A | 7/1990 | Linkow et al. | |
| 4,960,646 A | 10/1990 | Shimamune et al. | |
| 4,963,145 A | 10/1990 | Takagi et al. | |
| 4,969,906 A | 11/1990 | Kronman | |
| 4,988,299 A | 1/1991 | Branemark | |
| 5,000,685 A | 3/1991 | Brajnovic | |
| 5,030,096 A | 7/1991 | Hurson et al. | |
| 5,032,552 A | 7/1991 | Nonami et al. | |
| 5,034,352 A | 7/1991 | Vit et al. | |
| 5,039,546 A | 8/1991 | Chung et al. | |
| 5,071,351 A | 12/1991 | Green et al. | |
| 5,108,399 A | 4/1992 | Eitenmuller et al. | |
| 5,141,576 A | 8/1992 | Shimamune et al. | |
| 5,180,564 A | 1/1993 | Wahl et al. | |
| 5,188,800 A | 2/1993 | Green et al. | |
| 5,190,795 A | 3/1993 | Culler | |
| 5,195,891 A | 3/1993 | Sulc | |
| 5,199,873 A | 4/1993 | Schulte et al. | |
| 5,205,745 A | 4/1993 | Kamiya | |
| 5,205,921 A | 4/1993 | Shirkanzadeh | |
| 5,219,361 A | 6/1993 | von Recum et al. | |
| 5,222,983 A | 6/1993 | Schmitz et al. | |
| 5,242,706 A | 9/1993 | Cotell et al. | |
| 5,258,030 A | 11/1993 | Wolfarth et al. | |
| 5,263,986 A | 11/1993 | Noiles et al. | |
| 5,279,831 A | 1/1994 | Constantz et al. | |
| 5,297,963 A | 3/1994 | Dafatry | |
| 5,306,305 A | 4/1994 | Lee | |
| 5,310,464 A | 5/1994 | Redepenning | |
| 5,316,476 A | 5/1994 | Krauser | |
| 5,316,477 A | 5/1994 | Calderon | |
| 5,324,199 A | 6/1994 | Branemark | |
| 5,344,425 A | 9/1994 | Sawyer | |
| 5,344,457 A | 9/1994 | Pilliar et al. | |
| 5,360,448 A | 11/1994 | Thramann | |
| 5,362,237 A | 11/1994 | Chalifoux | |
| 5,366,374 A | 11/1994 | Vlassis | |
| 5,368,480 A | 11/1994 | Balfour et al. | |
| 5,368,483 A | 11/1994 | Sutter et al. | |
| 5,399,090 A | 3/1995 | Padros-Fradera | |
| 5,405,436 A | 4/1995 | Maurer et al. | |
| 5,427,754 A | 6/1995 | Nagata et al. | |
| 5,433,606 A | 7/1995 | Niznick et al. | |
| 5,441,536 A | 8/1995 | Aoki et al. | |
| 5,456,723 A | 10/1995 | Steinemann et al. | |
| 5,472,734 A | 12/1995 | Perrotta et al. | |
| 5,478,237 A | 12/1995 | Ishizasawa | |
| 5,484,286 A | 1/1996 | Hansson | |
| 5,489,210 A | 2/1996 | Hanosh | |
| 5,496,399 A | 3/1996 | Ison et al. | |
| 5,503,558 A | 4/1996 | Clokie | |
| 5,543,019 A | 8/1996 | Lee et al. | |
| 5,564,923 A | 10/1996 | Grassi et al. | |
| 5,571,017 A | 11/1996 | Niznick | |
| 5,571,188 A | 11/1996 | Ellingsen et al. | |
| 5,573,401 A | 11/1996 | Davidson et al. | |
| 5,588,838 A | 12/1996 | Hansson et al. | |
| 5,591,029 A | 1/1997 | Zuest | |
| 5,603,338 A | 2/1997 | Beaty | |
| 5,607,480 A | 3/1997 | Beaty | |
| 5,639,237 A | 6/1997 | Fontenot | |
| 5,816,811 A | 10/1998 | Beaty | |
| 5,863,201 A * | 1/1999 | Lazzara et al. | 433/201.1 |
| 5,876,453 A * | 3/1999 | Beaty | 433/201.1 |
| 5,989,027 A | 11/1999 | Wagner et al. | |
| 6,069,295 A * | 5/2000 | Leitao | 623/11.11 |
| 6,183,255 B1 * | 2/2001 | Oshida | 433/201.1 |
| 6,491,723 B1 | 12/2002 | Beaty | |
| 6,652,765 B1 | 11/2003 | Beaty | |
| 6,702,855 B1 | 3/2004 | Steinemann et al. | |
| 8,251,700 B2 * | 8/2012 | Robb et al. | 433/173 |
| 2001/0004711 A1 | 6/2001 | Lazzara et al. | |

FOREIGN PATENT DOCUMENTS

| | | |
|---|---|---|
| CH | 679117 A5 | 12/1991 |
| DE | 2 313 678 | 10/1972 |
| DE | 27 17 615 A1 | 10/1978 |
| EP | 202031 A2 | 11/1986 |
| EP | 212929 A2 | 3/1987 |
| EP | 0 213 836 | 11/1987 |
| EP | 0 409 810 | 1/1991 |
| EP | 455 929 A1 | 1/1991 |
| EP | 606 566 A1 | 7/1994 |
| EP | 0806211 B1 | 10/2002 |
| EP | 0987031 B1 | 4/2003 |
| EP | 1150620 B1 | 11/2003 |
| FR | 2 289 160 | 10/1974 |
| FR | 2 421 595 | 7/1979 |
| GB | 834256 | 5/1960 |
| GB | 2 045 083 A | 1/1984 |
| GB | 2252501 A | 8/1992 |
| JP | 63-147455 | 6/1988 |
| JP | 1148254 | 6/1989 |
| JP | 3146679 A2 | 6/1991 |
| JP | 62-34559 | 9/1994 |
| SE | 332 486 | 11/1971 |
| WO | 92/05745 | 4/1992 |

(56) References Cited

FOREIGN PATENT DOCUMENTS

| WO | 94/13334 A | 6/1994 |
|---|---|---|
| WO | 96/16611 | 6/1996 |
| WO | 01/56628 A1 | 8/2001 |

OTHER PUBLICATIONS

Adhesion of Bone to Titanium (Ref. 27), dated prior to May 2004.
Albrektsson, T., P.I. Branemark, H.A. Hansson & J. Lindstrom, "Osseointegrated Titanium Implants,", dated prior to May 2004.
An animal study of c.p. titanium screws with different surface topographies (Ref. D 32), dated prior to May 2004.
ASTM Designation F 86-84, "Standard Practice for Surface Preparation and Marking of Metallic Surgical Implants", dated prior to May 2004.
Baier, R. E., et al., "Implant Surface Preparation," International Journal of Oral & Maxillofacial Implants, vol. 3, pp. 9-20 (1988).
Baier, R. E., et al., "Surface Energetics and Biological Adhesion," International Symposium on Physicochemical Aspects of Polymer Surfaces, vol. 2, pp. 895-909, dated prior to May 2004.
Binon, P., "Evaluation of Machining Accuracy and Consistency of Selected Implants, Standard Abutments, and Laboratory Analogs," International Journal of Prosthodontics, vol. 8, pp. 162-178 (1995).
Bio Materials "Bone response to surface modified titanium implants: studies on electropolished implants with different oxide thicknesses and morphology", Larsson et al. 1994 vol. 15, No. 13, pp. 1062-1074.
Bio Materials "Bone response to surface-modified titanium implants: studies on the early tissue response to machined and electropolished implants with different oxide thicknesses", Larsson et al., 1996 vol. 17, No. 6 pp. 605-616.
Bowers, K., et al., "Optimization of Surface Micromorphology for Enhanced Osteoblast Responses In Vitro," International Journal of Oral & Maxillofacial Implants, vol. 7, No. 3, pp. 302-310 (1992).
Boyan et al., "Titanium Surface Roughness Alters Responsiveness of MG63 Osteoblast-Like Cells to $1\alpha,25$-(OH)2D3," J Miomed Mater Res, 39 (1998), pp. 77-85.
Branemark, P.I., et al., "Osseointegrated Implants in the Treatment of the Edentulous Jaw Experience From a 10 Year Period," Stockholm, Almqvist & Wiksell International (1977).
Buser et al., "Interface Shear Strength of Titanium Implants With a Sandblasted and Acid-Etched Surface: A Biomechanical Study in the Maxilla of Miniature Pigs," J Biomed Mater Res, 45 (1999), pp. 75-83.
Buser, D., et al., "Influence of Surface Characteristics on Bone Integration of Titanium Implants, A Histomorphometric Study in Miniature Pigs," Journal of Biomedical Materials Research, vol. 25, pp. 889-902 (1991).
C. de Putter et al., Implant Materials in Biofunction, "Removal Forces for Osseointegrated Titanium Implants" (Ref. 31), dated prior to May 2004.
Canadian Office Action for Canadian Patent No. 2,467,320 dated Jun. 19, 2008 (2 pages).
Carlsson L.; T. Rostlund; B. Albrektsson; T. Albrektsson "Removal Torques for Polished and Rough Titanium Implants," International Journal of Oral & Maxillofacial Implants, vol. 3, 21-24, 1988.
Edited by G. Heimke, U.Soltesz A.J.C. Lee, "The Influence of Various Titanium Surfaces on the Interface Shear Strength Between Implants and Bone," Clinical Implant Materials, Advances in Biomaterials, vol. 9, (1990) pp. 309-314.
Cochran et al., "Bone Response to Unloaded and Loaded Titanium Implants With a Sandblasted and Acid-Etched Surface: A Histometric Study in the Canine Mandible," J Biomed Mater Res, 40 (1998), pp. 1-11.
Cochran et al., "Evaluation of an Endosseous Titanium Implant With a Sandblasted and Acid-Etched Surface in the Canine Mandible: Radiographic Results," Clinical Oral Implants Research 1996: 7: 240-252.
Cook, S.; F. Georgette; H. Skinner; R. Haddad, Jr. "Fatigue properties of carbon- and porous-coated Ti-6A1-4V alloy," Journal of Biomedical Materials Research, vol. 18, 497-512, (1984).
Curtis, A. S. G., et al., "The Effects of Topographic and Mechanical Properties of Materials on Cell Behavior," Critical Reviews in Biocompatibility, vol. 5, Issue 4, pp. 343-362 (1990).
Dana C. Mears, B.M., B.Ch., Ph.D., M.R.C.P., F.R.C.S. (C), "Materials and Orthopaedic Surgery" (Ref. 42), dated prior to May 2004.
Daniel Buser, DDS, et al., "Removal Torque Values of Titanium Implants in the Maxilla of Miniature Pigs", pp. 611-619, dated prior to May 2004.
Das Prinzip der neuen Ledermann-Schraube (German Reference D3), dated prior to May 2004.
David E. Steflik, MS, EdD, et al., "A Comparative Investigation in Dogs: 2-Year Morphometric Results of the Dental Implant-Bone Interface", pp. 15-25, dated prior to May 2004.
David E. Steflik, MS, EdD, et al., "Histomorphometry of the Dental Implant-Bone Interface: One-Year Results of a Comparative Investigation in Dogs", pp. 501-511, dated prior to May 2004.
De Groot, K., et al., "Plasma Sprayed Coatings of Hydroxylapatite," Journal of Biomedical Materials Research, vol. 21, pp. 1375-1381 (1987).
Decision on Appeal from the U.S. Patent & Trademark Office in U.S. Appl. No. 09/237,605 dated May 30, 2007.
Decision on Request for Rehearing in U.S. Appl. No. 09/237,605 dated Nov. 13, 2007.
Denar Introduces Steri-Oss: The First Complete Oral Rehabilitation Implant System, dated prior to May 2004.
Design and Surface Characteristics of 13 Commercially Available Oral Implant Systems, Int. J. Oral Maxillofactial Implants, (1993), 8:622-633.
Eberhardt, A., et al., "Effects of Precoating Surface Treatments on Fatigue of Ti-6A1-4V," Journal of Applied Biomaterials, vol. 6, pp. 171-174 (1995).
Effect of a Glycoprotein Monomolecular Layer on the Integration of Titanium Implants in Bone (Ref. D48), dated prior to May 2004.
Gomez-Roman, German, et al., "The Frialit-2 Implant System: Five-Year Clinical Experience in Single-Tooth and Immediately Postextraction Applications," The International Journal of Oral & Maxillofacial Implants, vol. 12, No. 3, pp. 299-309 (1997).
Gotfredsen, K., et al., "Histomorphometric and Removal Torque Analysis for TiO2-Blasted Titanium Implants" Clinical Oral Impl. Res., Feb. 6, 1992, pp. 77-84.
Ingemar, Olefjord, et al., "Surface Analysis of Four Dental Implant Systems," International Journal of Oral & Maxillofacial Implants, vol. 8, No. 1, pp. 32-40 (1993).
Ion-Beam-Sputter Modification of th, e Surface Morphology of Biological Implants, J.Vac. Soc. Technol., vol. 14, No. 1, Jan./Feb. 1977, pp. 326-331.
Journal of Materials Science Materials in Medicine "Bone response to surface modified titanium implants—studies on the tissue response after 1 year to machined and electropolished implants with different oxide thicknesses" (1997), , pp. 721-729.
Karagianes, M. T., D.V.M., "Porous Metals as a Hard Tissue Substitute," Biomat. Med. Dev., Art. Org., vol. 1, No. 1, pp. 171-181 (1973).
Kasemo, B., et al., "Metal Selection and Surface Characteristics," Tissue-Integrated Prostheses Osseointegration in Clinical Dentistry (Quintessence Books), pp. 99-116 (1985).
Kevin A. Thomas et al., "An evaluation of variables influencing implant fixation by direct bone appostion" (Ref. 46), dated prior to May 2004.
Kiesweiter et al., "Surface Roughness Modulates the Local Production of Growth Factors and Cytokines by Osteoblast-Like MG-63 Cells," Journal of Biomedical Materials Research, vol. 32, (1996), pp. 55-63.
Klokkevold, P., et al., "Evaluation of a New Chemically Enhanced Implant Surface by Torque Removal Tests in the Rabbit Femur," Clinical Oral Implants Research (1997).
Lazzara, R., et al., "Retrospective Multicenter Analysis of 3I Endosseous Dental Implants Placed Over a Five Year Period," Clinical Oral Implants Research, vol. 7, pp. 73-83 (1996).
Ledermann et al., "The Ha-TI Implant," Schweiz Monatsschr Zahnmed, vol. 101, No. 5, 7 pages (May 1991).

(56) References Cited

OTHER PUBLICATIONS

Martin et al., "Effect of Titanium Surface Roughness on Proliferation, Differentiation, and Protein Synthesis of Human Osteoblast-Like Cells (MG63)," Journal of Biomedical Materials Research, vol. 29, 389-401 (1995), pp. 389-402.
Messersmith, P., et al., "Stress Enhancement and Fatigue Susceptibility of Porous Coated Ti-6A1-4V Implants: An Elastic Analysis," Journal of Biomedical Materials Research, vol. 24, pp. 591-604 (1990).
Microfocus (Ref. D50), dated prior to May 2004.
Microfocus (Ref. D51), dated prior to May 2004.
Notice of Opposition of EP Patent No. 04011563.6 dated Jun. 18, 2008 (1 page).
Notice of Opposition of EP Patent No. 04011563.6 dated May 23, 2008 (29 pages).
Orale Implantologie (Ref. 36), dated prior to May 2004.
Paragon Technology Report (Oct. 1997).
Patrick J. Henry, B.D.Sc., M.S.D., F.R.A.C.D.S., "Comparative Surface Analysis of Two Osseointegrated Implant Systems" (Ref. D19), dated prior to May 2004.
Per-Ingvar Branemark, M.D., Ph.D., "Tissue-Integrated Prostheses" (Ref. 43), dated prior to May 2004.
Persson LG, Berglundh T, Sennerby L, Lindhe J., "Re-Osseointegration After Treatment of Peri-Implantitis at Different Implant Surfaces. An Experimental Study in the Dog," Clin Oral Impl. Res., 12 (2001), pp. 595-603.
Philippe D. Ledermann, Dr. med. dent. "Heute so zuverlässig wie vor 50 Jahren" German (Ref. D4), dated prior to May 2004.
Philippe D. Ledermann, Dr. med. dent., "Die Quintessenz" (Ref. 26), dated prior to May 2004.
Philippe D. Ledermann, Dr. med. dent., "Swiss Dent" (Ref. D25), dated prior to May 2004.
Predecki, Paul, et al., "Attachment of Bone to Threaded Implants by Ingrowth and Mechanical Interlocking," Journal of Biomedical Materials Research, vol. 6, pp. 401-412 (1972).
Price List and Catalog, Friadent, 35 pages (Sep. 2000).
Price List, Friatec, 40 pages (Oct. 1998).
Product Literature for Frialit®-2 Implant System, Friadent, 12 pages (Feb. 1999).
Product Literature for Frialit®-2 Implant System, Interpore International and Friatec, 3 pages (1996).
Product Literature for Frialit®-2, Abridged Directions for Use, Interpore International and Friatec, 20 pages (believed to be 1996 or 1997).
Product Literatyre for Frialit®-2, Friadent, 2 pages (believed to be 2000).
Request for Rehearing of Decision on Appeal filed by Applicant in U.S. Appl. No. 09/237,605 dated Jul. 30, 2007.
S.A.V. Swanson, DSc (Eng), PhD, DIC, ACGI, MIMechE, et al. "The Scientific Basis of Joint Replacement" (Ref. D41), dated prior to May 2004.
Schulte, J., "External Hex Manufacturing Tolerances of Six Implant Systems: A Pilot Study," Implant Dentistry, pp. 51-53 (Spring 1994).
Schute, W., et al., "The First 15 years of the Tuebinger Implant and Its Further Development to the Frialit®-2 System," Zeitschrift fur Zahnarzliche Implantologie, Band VIII, cover page, pp. 3-22 (Feb. 1992).
Schwartz et al., "Effect of Titanium Surface Roughness on Chonrocyte Proliferation, Matrix Production, and Differentiation Depends on the State of Cell Maturation," Journal of Biomedical Materials Research, vol. 30, 145-155 (1996), pp. 145-155.
Short-Term Plasma-Cleaning Treatments Enhance In Vitro Osteoblast Attachment to Titanium, Journal of Oral Implantology, vol. XVIII, No. 2, pp. 130-137 (1992).
Shultz, R. R., et al., "A Study of Fatigue Properties of Hydroxylapatite Coated Titanium Alloy Implant Materials," Department of Biomedical Engineering, Memphis State University, dated prior to May 2004.
Smith, Todd, "The Effect of Plasma-Sprayed Coatings on the Fatigue of Titanium Alloy Implants" (Ref. 29), dated prior to May 2004.
Sorensen, J., et al., "Comparison of Interface Fidelity of Implant Systems," Journal of Dental Research, vol. 70, No. 540, Abstract No. 2191 (1991).
Standard Recommended Practice for Descaling and Cleaning Titanium and Titanium Alloy Surfaces (Ref. D6), dated prior to May 2004.
Stephen D. Cook, Ph.D. et al., "Interface Mechanics and Histology of Titanium and Hydroxylapatite-Coated Titanium for Dental Implant Applications" (Ref. 47), dated prior to May 2004.
Step-Screw Implant, Dental Products Report, Mar. 1993.
Strauman Literature Abstracts, dated prior to May 2004.
Strauman SLA: Reducing healing time further, dated prior to May 2004.
Sullivan, Daniel, et al., "Preliminary Results of a Multicenter Study Evaluating Chemically-Enhanced Pure Titanium Implants," Journal of Prosthetic Dentistry (1997).
Sutter et al., "The New Restorative Concept of the ITI Dental Implant System: Design and Engineering," vol. 13, No. 5, pp. 408-413 (1993).
The Dependence of the Removal Torque of a Leg Screw Surface and implantation Time (Ref. D30), dated prior to May 2004.
The Influence of Implant Surface on Hard- and Soft Tissue Integration Friatec website, 11 pages (written after Jun. 6, 1998).
Thomas, K. A., et al., "The Effect of Surface Macrotexture and Hydroxylapatite Coating on the Mechanical Strengths and Histologic Profiles of Titanium Implant Materials," Journal of Biomedical Materials Research, vol. 21, pp. 1395-1414 (1987).
Titan (Ref. D35), dated prior to May 2004.
University of Bern (Switzerland), Clinic for Dental Maintenance (Schweizerisch Monatschrift für Zahnheilkunde, vol. 86, No. 7, Jul. 1976, pp. 713-727).
W. Eugene Roberts, D.C.S., Ph.D., et al., "Osseous adaptation to continuous loading of rigid endosseous implants" (Ref. D7), dated prior to May 2004.
W. M. Murphy, "Tissue Reaction of Rats and Guinea-Pigs to Co—Cr Implants With Different Surface Finishes" (Ref. D8), dated prior to May 2004.
Weinlaender, M., et al., "Histomorphometry of Bone Apposition Around Three Types of Endosseous Dental Implants," International Journal of Oral & Maxillofacial Implants, vol. 7, No. 4, pp. 491-496 (1992).
Wennerberg, A., et al., "Design and Surface Characteristics of 13 Commercially Available Oral Implant Systems," International Journal of Oral & Maxillofacial Implants, vol. 8, No. 6, pp. 622-633 (1993).
Wheeler, K. R., et al., "Porous Metals as a Hard Tissue Substitute. Part II. Porous Metal Properties," Biomat. Med. Dev., Art. Org., vol. 1, No. 2, pp. 337-348 (1973).
Wheeler, Stephen L., "Eight Year Clinical Retrospective Study of Titanium Plasma-Sprayed and Hydroxyapatite-Coated Cylinder Implants," International Journal of Oral & Maxillofacial Implants, vol. 11, No. 3, pp. 340-350 (1996).
Widmer, Martin, 'Kontrolle der Oberflachenqualitat von anodisierten Titan-Implantaten mittels Reflexionsspektroskopie,' dated Feb. 1998 (50 pages).
Wong, M., et al., "Effect of Surface Topology on the Osseointegration of Implant Materials in Trabecular Bone," Journal of Biomedical Materials Research, vol. 29, pp. 1567-1575 (1995).
Yue, S., et al., "The Fatigue Strength of Porous-Coated Ti-6%A1-4% V Implant Alloy," Journal of Biomedical Materials Research, vol. 18, pp. 1043-1058 (1984).
Orale Implantologie (Ref. D58), dated prior to May 2004.

\* cited by examiner

SURFACE TREATMENT PROCESS FOR IMPLANTS MADE OF TITANIUM ALLOY

CROSS-REFERENCE TO RELATED APPLICATIONS

This application is a continuation of U.S. patent application Ser. No. 10/843,916, filed May 12, 2004, which claims priority of provisional patent application 60/471,463, filed May 16, 2003, both of which are hereby incorporated by reference in their entireties.

FIELD OF THE INVENTION

This invention relates generally to the surface of metal implants, such as those placed in the human body.

BACKGROUND OF THE INVENTION

This invention principally relates to the surface of titanium alloy dental implants, although it has application to other types of implants made of titanium alloys. More specifically, the invention relates to roughened surfaces provided on dental implants to improve the osseointegration of the implant surface with the bone, thereby shortening the time between initial insertion of the implant and the installation of a prosthetic tooth.

Various techniques have been suggested for roughening implants, each producing a unique surface. One approach has been to apply materials to the surface of the implant, for example hydroxyapitite, a material that is considered to improve the bonding of the implant to bone because the hydroxyapitite is chemically related to bone. In a related approach, titanium particles have been sprayed onto a titanium implant to roughen the surface. Anodization to add titanium oxides to the surface has also been proposed. Roughening also can be done by removing some of the surface. Grit blasting with fine particles has been proposed to create dents and to abrade away some of the surface. Another method is the use of acid etching to create a roughened surface. At least one supplier of dental implants has proposed grit blasting to create a coarse roughened surface, followed by acid etching to form a superimposed fine roughening.

Etching the surface of titanium with acids has been included in many processes proposed for manufacturing dental implants. In many cases, only general reference to selecting from a list of mineral acids, in other instances specific acids are used. For example, Toho Titanium Co. disclosed in Japanese Published Patent Application JP3146679A1 a two step treatment in which aqueous hydrofluoric acid was used to etch the surface, followed by a second treatment with a solution hydrofluoric acid and hydrogen peroxide. Another example is found in U.S. Published Application 2003/0135282A1, in which an implant is treated with a sequence of three acids—hydrofluoric, sulfuric and hydrochloric acid. The etched surface is coated with plasma before use to improve integration with bone.

In a series of U.S. patents, including U.S. Pat. Nos. 5,603,338; 5,876,453; 5,863,201; and 6,652,765 assigned to Implant Innovations Inc., a unique two-step acid treatment was disclosed, which is used on dental implants to produce an Osseotite® surface. The first acid treatment uses aqueous hydrofluoric acid to remove the "native oxide", that is, the titanium oxide found on titanium metal surfaces. Removing the native oxide makes the metal surface more accessible to etching by other acids, assuring uniform etching of the titanium surface. Other methods of removing the native oxide could be used, such as plasma treatment, but the initial treatment with aqueous hydrofluoric acid was preferred. The second acid treatment preferably used a mixture of hydrochloric and sulfuric acids to etch the exposed titanium surface. A relatively fine etching was achieved, having peak-to-valley heights of 10 µm or less. The peak-to-peak distance typically is about 1-3 µm. This Osseotite® surface has achieved commercial success, having reduced the time required for osseointegration of the titanium implant with bone.

Previous U.S. patents have shown the titanium surface obtained by scanning electron microscopy (SEM). Another method of describing the surface is surface mapping microscopy (SMM), which produces a computer-generated three-dimensional picture of the region being examined, and several calculated measures of the roughness of the surface. It will be understood by those skilled in the art that acid treatment produces a surface that appears very uniform to the naked eye, but contains variations that become evident only when greatly magnified, as in the photomicrographs. Each region will not be precisely the same as the others, but nevertheless, the variations are small and fall within the general limits discussed above. By carefully controlling the treatment process, each implant has substantially the same surface.

It has more recently been found that, while a consistent response to the two-step acid treatment is obtained on commercially pure titanium, the same treatment process produces non-uniform results on titanium alloys. Because titanium alloys have some benefits over commercially pure titanium, it would be desirable if the topography of the Osseotite® surface were to be duplicated on a titanium alloy surface. To achieve this goal, the inventors found that the process used for commercially pure titanium required unexpected revisions to achieve the desired surface on titanium alloys. Their new process will be described in detail below.

SUMMARY OF THE INVENTION

A process for producing on a titanium alloy a desired surface topography similar to the Osseotite® surface removes the native oxide on the titanium alloy and thereafter, and before the titanium alloy reoxidizes significantly, the surface is etched in an aqueous solution of hydrofluoric and hydrochloric acids to produce the desired surface. The native oxide maybe removed by immersing for about 40 to 60 seconds in an aqueous solution of hydrofluoric acid containing about 7.9 to 9.0 wt % hydrofluoric acid. In a preferred embodiment, the surface is etched for about 19-21 minutes at room temperature in an acid mixture containing from about 0.053 to about 0.105 wt % hydrofluoric (HF) acid and from about 19 to about 21 wt % hydrochloric (HCl) acid. The conditions for both acid treatments are chosen to provide the desired surface topography, while minimizing the loss of titanium metal.

In one specific embodiment, the native oxide is removed by immersing the implant in an 8.45 wt % HF solution at ambient temperature for 45 seconds. After rinsing to remove the residual acid, the implant is immersed for 19.5 minutes at ambient temperature in a 20 wt % HCl solution containing 0.0845 wt % HF.

The conditions for both acid treatments are chosen to provide the desired surface topography, while minimizing the loss of titanium metal.

In one aspect, the invention is a dental implant that has been treated according to the process described above to provide the desired surface topography in predetermined regions of the implant.

DETAILED DESCRIPTION OF THE PREFERRED EMBODIMENTS

Titanium and Titanium Alloys

Although other metals, and ceramics have been proposed for use in dental implants, titanium has been generally used. Particularly commercially pure titanium, which contains trace amounts of carbon, iron, oxygen, hydrogen, and nitrogen. Titanium alloys have also been used since they are stronger than the commercially pure grades of titanium. One commonly used titanium alloy, Ti/6Al/4V, contains 6 wt % aluminum and 4 wt % vanadium, hereafter referred to as Ti 6/4.

A characteristic of titanium and its alloys is the rapid formation of tenacious titanium oxide films on the surface, a feature which contributes to titanium's resistance to corrosion. This oxide film is considered to be a combination of various oxides of titanium, including $TiO$, $TiO_2$, $Ti_2O_3$, and $Ti_3O_4$. It has been referred to the "native oxide" film. Measurement of the native oxide film by Auger spectrometer indicates that it typically has a depth of 70 to 150 Angstroms.

As previously disclosed, removing the native oxide is important if a uniformly roughened surface is to be produced by acid etching. Experience has shown that most acids are not capable of removing the native oxide sufficiently so that a uniform roughness can be produced. Titanium surfaces are often pickled in mixtures of hydrofluoric acid and nitric acids to clean the surface. Aqueous solutions of hydrofluoric acid alone, without the addition of oxidizing acids such as nitric acid, are very aggressive toward titanium and its native oxide film. A relatively brief exposure to a dilute solution of hydrofluoric acid will remove the native oxide. Since after removing the native oxide, the hydrofluoric acid will begin to consume the metal as well, an undesirable result, the titanium implant is removed from the acid and rinsed to stop further attack. However, as is well known, the titanium metal surface will begin to oxidize quickly. Consequently, the exposed metal surface should be protected against oxygen exposure until the titanium implant is immersed in an acid bath to uniformly etch the surface, creating the desired surface topography. Other methods of removing the native oxide could be used, such as plasma treatment, but the use of hydrofluoric acid is preferred.

Figure 1A:
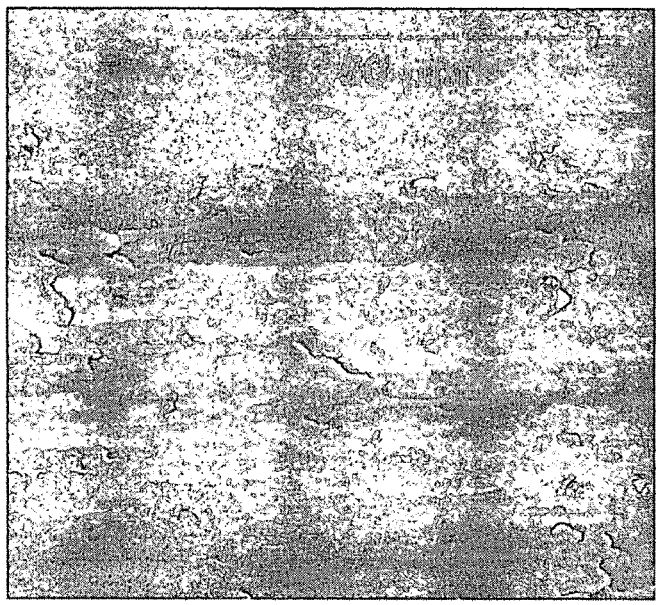
FIG. 1A shows a commercially pure titanium machined surface.
Figure 1B:
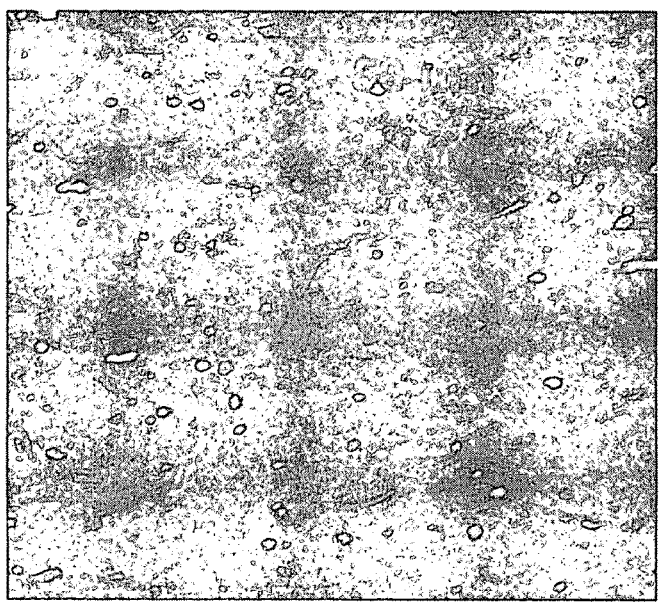
FIG. 1B shows the surface of FIG. 1A after being treated with HF

The rate at which titanium is etched depends on the concentration of the hydrofluoric acid. A hydrofluoric acid solution containing about 15 vol. % of 49 wt % hydrofluoric acid was found to permit complete removal of the native oxide within about one-half minute, but with minimal consumption of the metal. This is illustrated in FIGS. 1A and B which show at 2000× magnification the surface of a commercially pure titanium metal dental implant after machining (producing macro-features such as threads or grooves) and then after being exposed to hydrofluoric acid to remove the native oxide. The machining marks have disappeared and the hydrofluoric acid has left the titanium grains exposed after the native oxide has been removed and some of the grain boundary material has been removed.

Figure 1C:
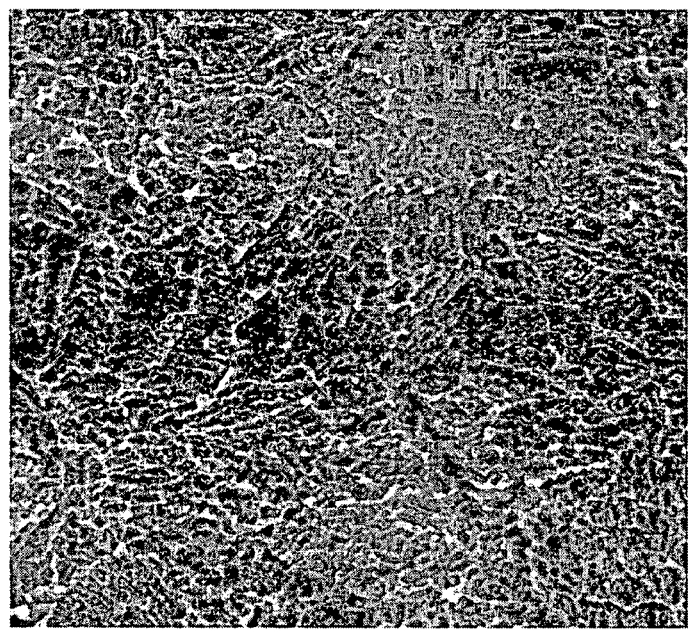
FIG. 1C shows the surface of FIG. 1B after being etched with HCl and H2SO4 so as to produce an Osseotite® surface on pure titanium.
Figure 1D:
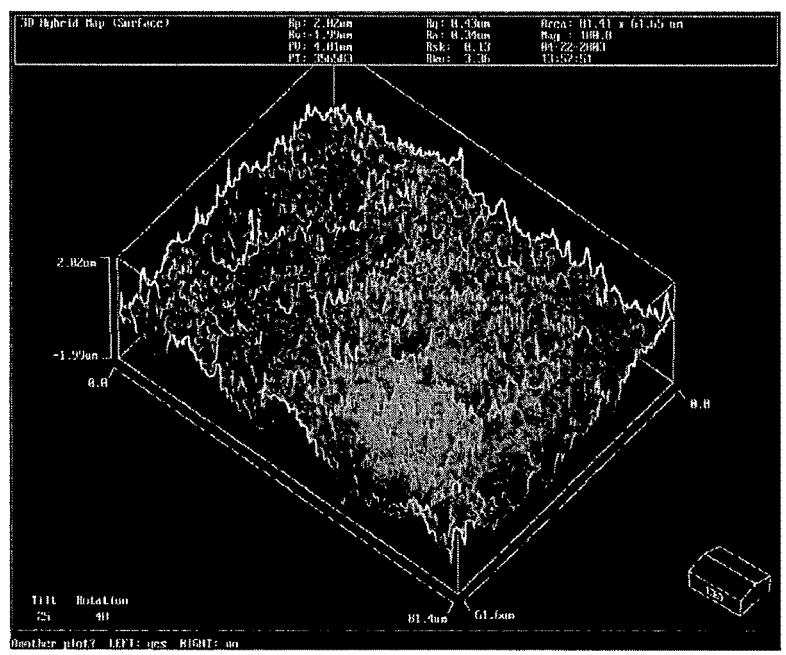
FIG. 1D is a surface map of the Osseotite® surface of FIG. 1C.

In FIG. 1C, the surface of the commercially pure titanium (after native oxide has been removed) has been etched with a solution of 19.55 wt % hydrochloric acid and 72.29 wt % sulfuric acid at 60-70° C. for about 7 minutes. This desirable surface topography has been clinically demonstrated to achieve enhanced osseointegration. Implants having this surface are sold under the Osseotite® trademark by the assignee of the present invention. This desirable surface has a generally uniform set of sharp peaks with a maximum peak-to-valley height of 10 μm or less. The average peak-to-peak distance is about 1-3 μm. The result of a typical examination of an Osseotite® surface by surface mapping microscopy is shown in FIG. 1D.

FIGS. 1A-1D illustrate the process and results produced on a commercially pure titanium dental implant. Clinical success of the Osseotite® surface in improving osseointegration of the implants has been confirmed and it is well accepted in the marketplace. Therefore, the present inventors had expected to create the same surface topography on titanium alloy Ti 6/4 using the same treatment. However, they were surprised to discover that the process providing uniform results on commercially pure titanium failed to produce the characteristic surface topography when applied to Ti 6/4 alloy.

Other etching solutions were tested. In some instances, a surface similar to the Osseotite® surface was obtained, but in other cases, acid etching was ineffective. It was found also that the effect on Ti 6/4 alloy varied from batch to batch, so that each batch had to be tested to determine its suitability. After further investigation of this problem, the inventors found that certain acid etching solutions were capable of consistently producing the desired surface on Ti 6/4 alloy.

Acid Etching of Ti 6/4 Alloy

FIGS. 1E, and 2C-E, 3A-E, 4A, B, and 5A-D illustrate the results of some of the acids tested on Ti 6/4 E.L.I. alloy, as defined by ASTM B348 Grade 23 or ASTM F136. In each case, the implants had been given the same treatment in a hydrofluoric acid solution to remove the native oxide on the surface. In particular, the implants were immersed in 8.45 wt % hydrofluoric acid at room temperature. The results of the etching processes shown in FIGS. 1E, and 2C-E, 3A-E, 4A, B, and 5A-D can be compared with FIG. 1C, the Osseotite® surface produced on commercially pure titanium metal by an acid treatment with an initial mixture of 19.55 wt % hydrochloric acid and 72.29 wt % sulfuric acid at 60-70° C. for 7 minutes.

Experiments were carried out with a series of acid compositions, the results being shown in Figures. The acid compositions and treatment conditions are summarized in the following table.

TABLE 1

| | | Native Oxide Removal Treatment | | Etching Acid Composition[1] | | | | | |
|---|---|---|---|---|---|---|---|---|---|
| FIG. | Ti: | 8.45 wt % HF | Time, min. | HF | HCl | $H_2SO_4$ | $HNO_3$ | Time min. | Temp ° C. |
| 1C | CP | Yes | 1.0 | — | 19.55 | 77.29 | — | 7 | 60-70 |
| 1E | 6/4 | Yes | 1.0 | — | 19.55 | 77.29 | — | 7 | 60-70 |
| 2A | 6/4 | No | — | 0.284 | 1.062 | — | 2.297 | 1 | 61 |
| 2B | 6/4 | No | — | 0.284 | 1.062 | — | 2.297 | 8 | 61 |
| 2C | 6/4 | Yes | 0.5 | 0.284 | 1.062 | — | 2.297 | 0.5 | 61 |
| | | | | — | 19.55 | 77.29 | — | 1.0 | 61 |
| 2D | 6/4 | Yes | 0.5 | 0.284 | 1.062 | — | 2.297 | 0.5 | 61 |
| | | | | — | 19.55 | 77.29 | — | 7 | 61 |
| 2E | 6/4 | Yes | 0.17 | 0.284 | 1.062 | — | 2.297 | 1.5 | 61 |
| | | | | 1.143 | — | — | 1.923 | 1.5 | ambient |
| 3A | 6/4 | Yes | 1.0 | 0.284 | 1.062 | — | 2.297 | 7 | ambient |
| 3B | 6/4 | Yes | 2.5 | 0.284 | 1.062 | — | 2.297 | 7 | ambient |
| 3C | 6/4 | Yes | 1.0 | 0.284 | 1.062 | — | 2.297 | 10 | ambient |
| 3D | 6/4 | Yes | 2.5 | 0.284 | 1.062 | — | 2.297 | 10 | ambient |
| 3E | 6/4 | Yes | 2.5 | 0.284 | 1.062 | — | 2.297 | 10 | ambient |
| 4A | 6/4 | Yes | 1.5 | — | 20 | — | — | 14 | ambient |
| 4B | 6/4 | Yes | 1.5 | — | 20 | — | — | 21 | ambient |
| 5A | 6/4 | Yes | 1.0 | 0.26 | 20 | — | — | 20 | ambient |
| 5B | 6/4 | Yes | 1.0 | 0.175 | 20 | — | — | 20 | ambient |
| 5C | 6/4 | Yes | 1.0 | 0.09 | 20 | — | — | 20 | ambient |
| 5D | 6/4 | Yes | 1.0 | 0.09 | 20 | — | — | 20 | ambient |

[1]wt % acid, remainder water

The above table generally follows the progress of experiments carried out to determine the acid etching needed to produce the desired surface topography on Ti 6/4 alloy. To produce the surface of FIG. 1C, the native oxide on the commercially pure titanium was removed by exposure to an 8.45 wt % HF solution for 1 minute at ambient temperature. After rinsing in deionized water containing baking soda to neutralize the residual acid and a further rinse in deionized water, the titanium was immersed in an aqueous solution of 19.55 wt % HCl and 77.29 wt % $H_2SO_4$ for 7 minutes at 60-70° C. to produce a uniformly roughened surface, i.e. the Osseotite® surface.

Figure 1E:
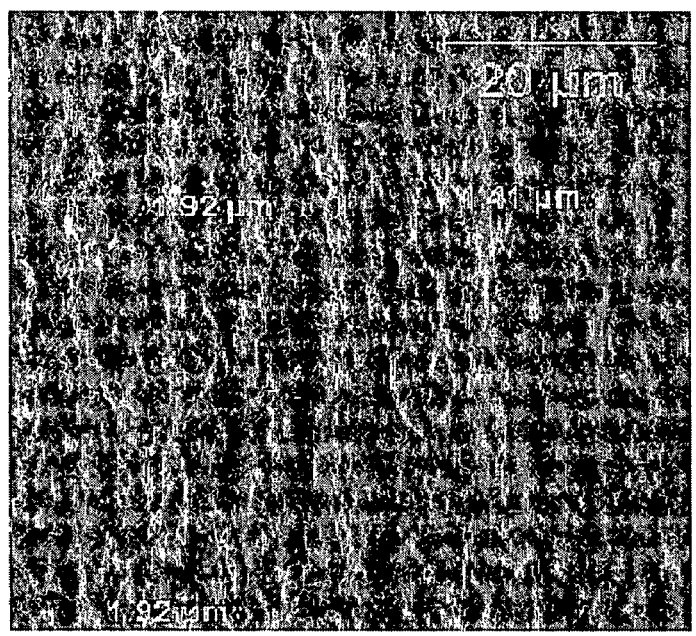
FIG. 1E shows the effect of the treatment of FIG. 1A-C on Ti 6/4 alloy.

FIG. 1E illustrates the surprising result when the same procedure was carried out on Ti 6/4 alloy. As will be seen in the photograph, the characteristic Osseotite surface was not obtained on Ti 6/4 alloy. The machining marks were still visible. It was concluded that a different etching process was needed for use with Ti 6/4 alloy if the Osseotite® surface was to be provided on the Ti 6/4 alloy.

Figure 2A:
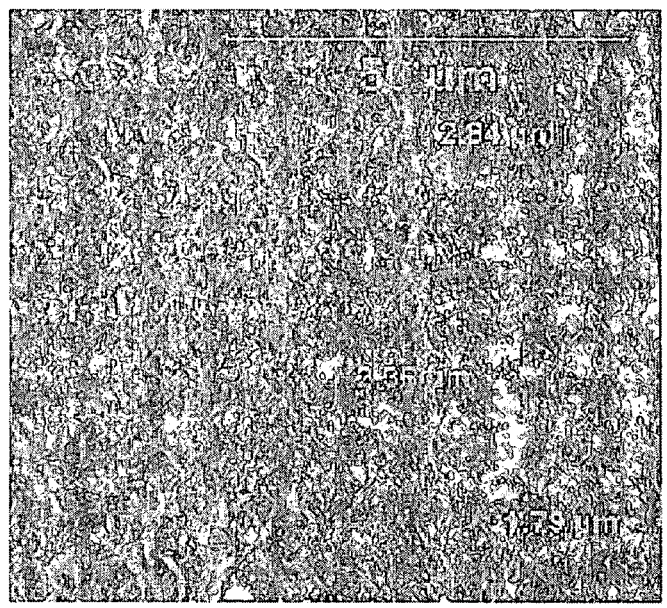
FIG. 2A-E show several etching processes on Ti 6/4 alloy.
Figure 2B:
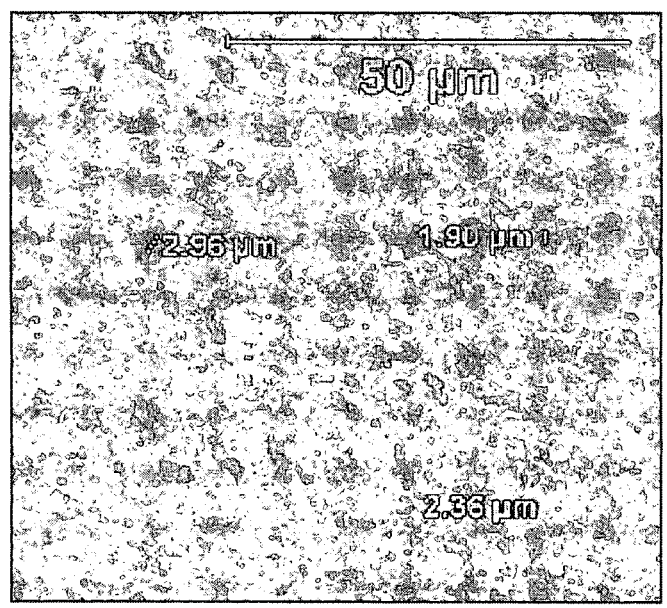

FIGS. 2A-E show the results obtained when two known etching acid mixtures were used. One was Keller's solution, containing HF, $HNO_3$, and HCl, and the second was Kroll's solution, containing HF and $HNO_3$. The compositions used are shown in Table 1 above. FIGS. 2A and 2B show that Keller's solution alone did not produce the Osseotite surface, although some pitting can be seen. Since the pre-treatment with HF solution to remove the native oxide was not done, it is presumed that the native oxide interfered with the attempted etching with Keller's solution.

Figure 2C:
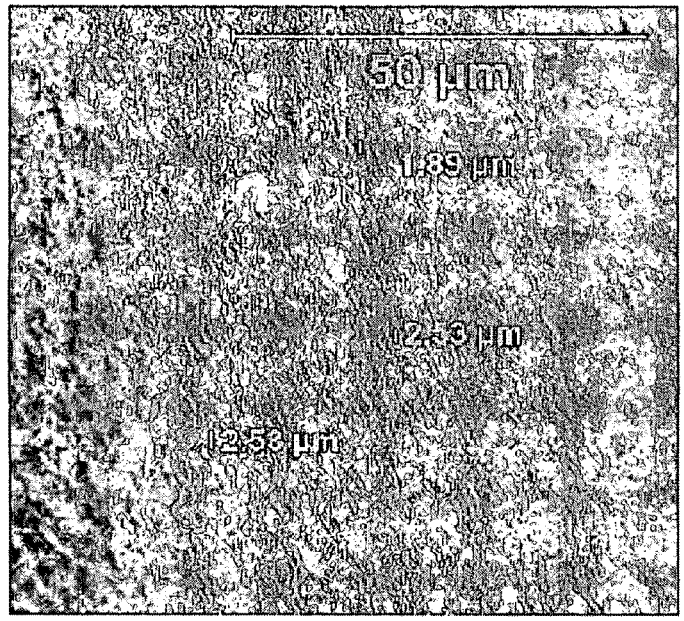
Figure 2D:
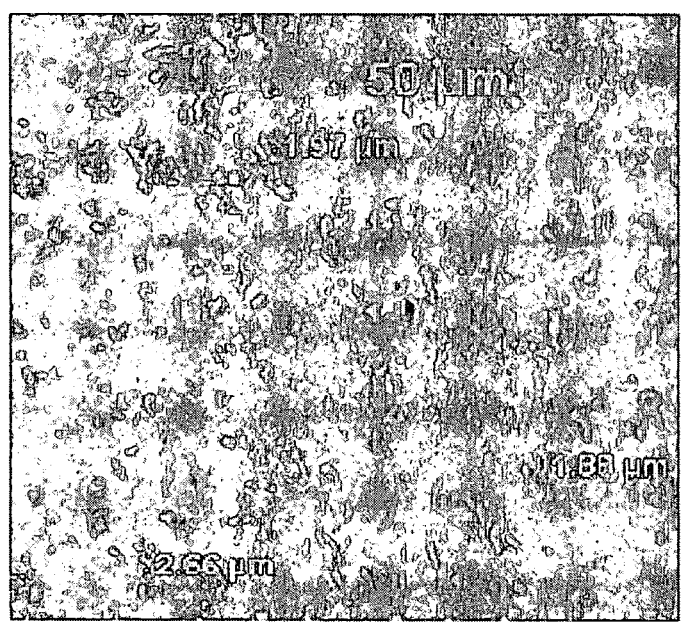
Figure 2E:
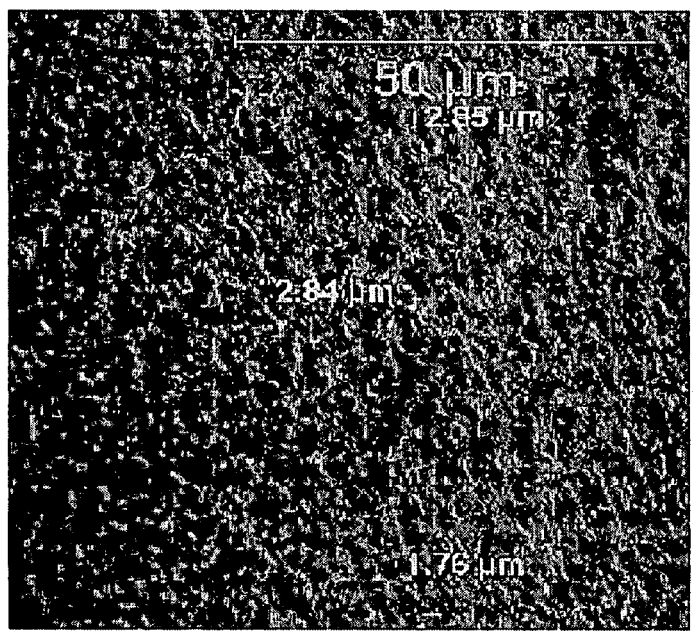
Figure 3A:
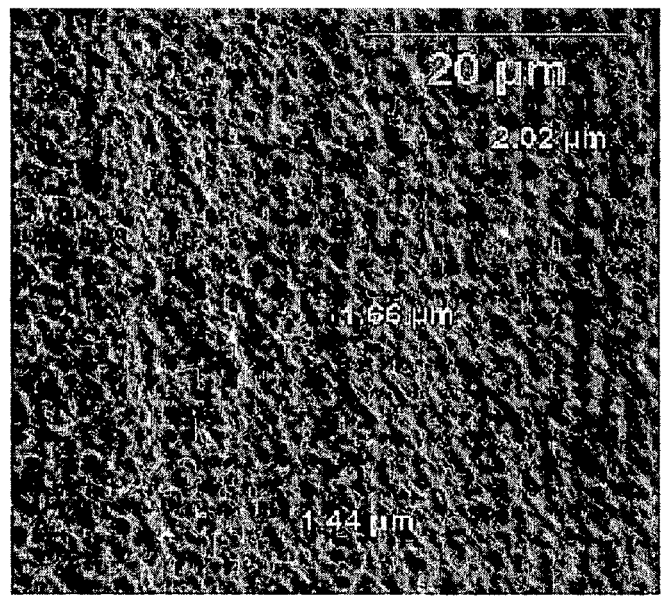
FIG. 3A-E show the effect of etching with Keller's reagent and Kroll's reagent.
Figure 3B:
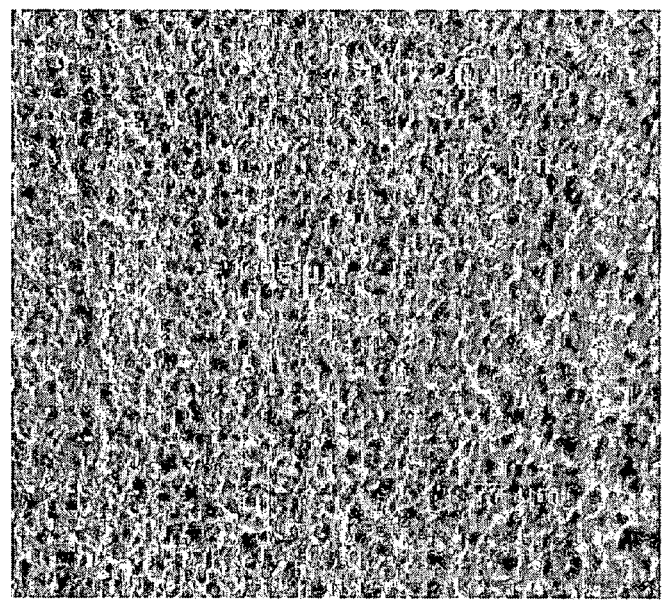
Figure 3C:
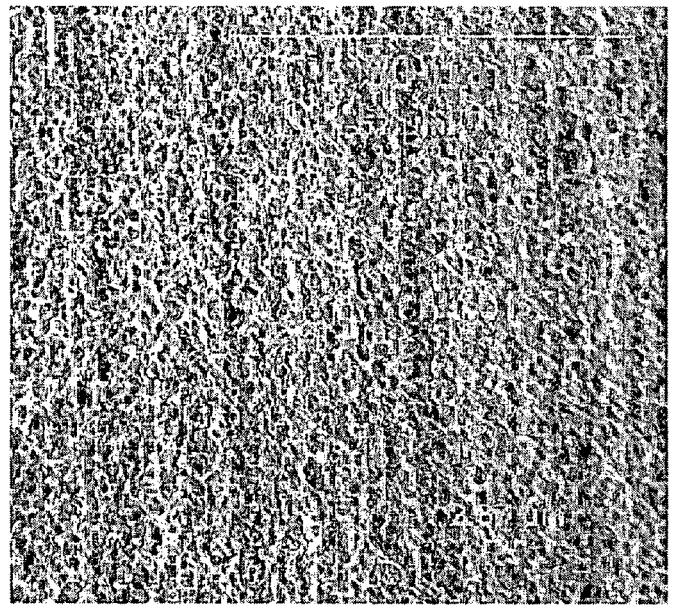
Figure 3D:
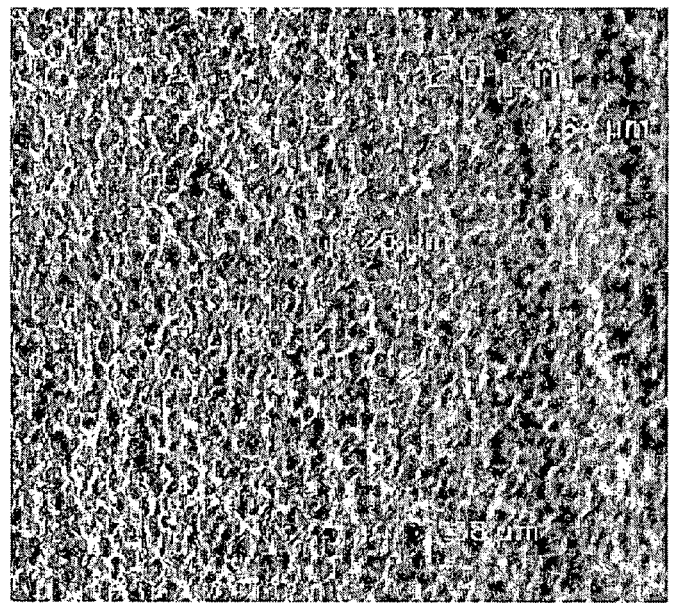
Figure 3E:
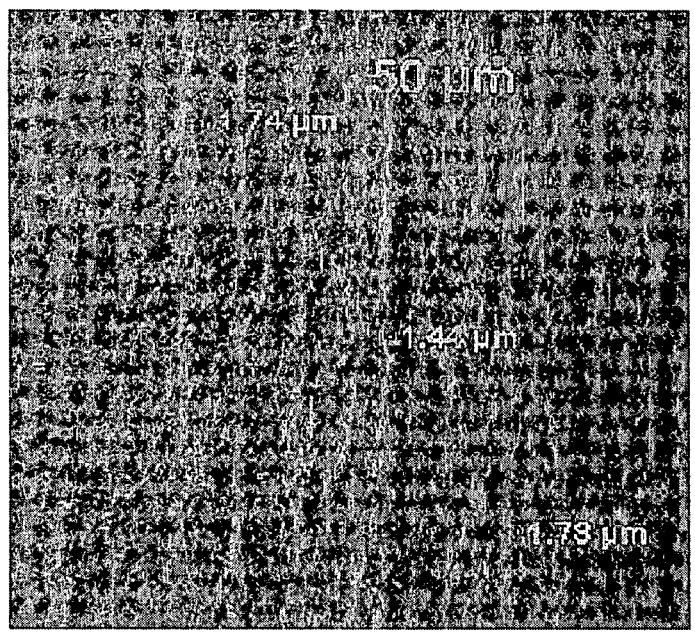

FIGS. 2C to 2E show the results achieved when the native oxide was removed by pre-treatment with an HF solution and thereafter the titanium surface was exposed to two acid solutions in sequence. In FIGS. 2C and 2D, Keller's solution was used, followed by the mixture of HCl and $H_2SO_4$, known to be successful in etching chemically pure titanium. In FIG. 2E, Keller's solution was used first, followed by immersion of the Ti 6/4 alloy in Kroll's solution. None of these tests produced a surface topography like that shown in FIG. 1C on the Ti 6/4 alloy.

FIGS. 3A-3E show the results obtained when the native oxide was removed with an HF solution, and Keller's solution was used for etching, but at ambient temperature rather than at 61° C. previously used. It was found that this process was capable of providing a surface similar to FIG. 1C on some samples of Ti 6/4 alloy, but not on others (compare FIG. 3 D with FIG. 3 E). The difference in response of the samples appeared to be associated with the machining or the alloy heat (i.e., the conditions associated with a specific batch of titanium alloy). Therefore, additional experimentation was undertaken. However, it was concluded that etching with Keller's solution may be useful also, provided that control of the quality of the Ti 6/4 alloy can be achieved.

Figure 4A:
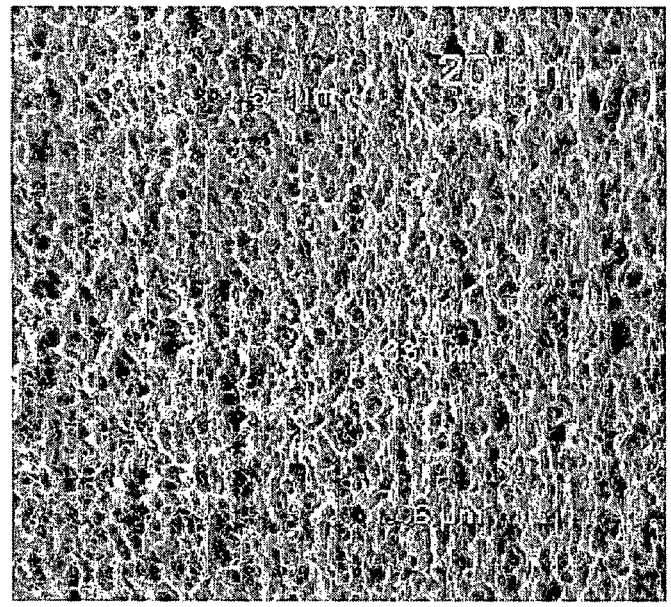
FIG. 4A-B show the effect of etching with HCl alone.
Figure 4B:
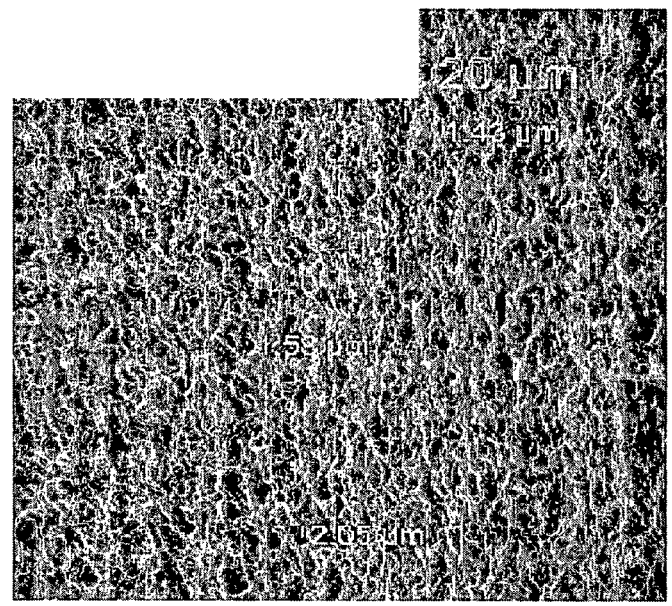
Figure 5A:
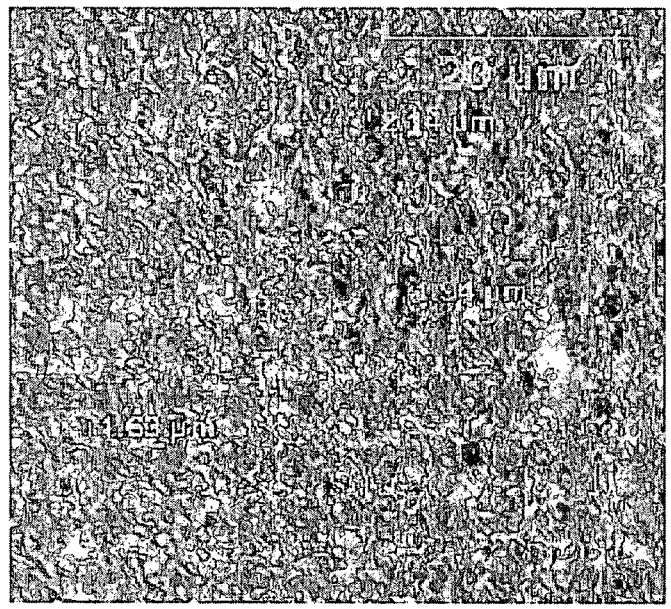
FIG. 5A-D show the effect of etching with HCl plus HF.
Figure 5B:
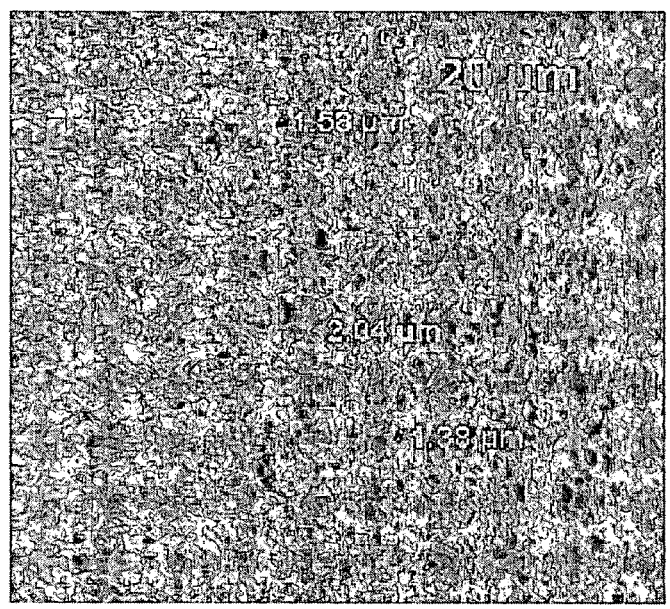
Figure 5C:
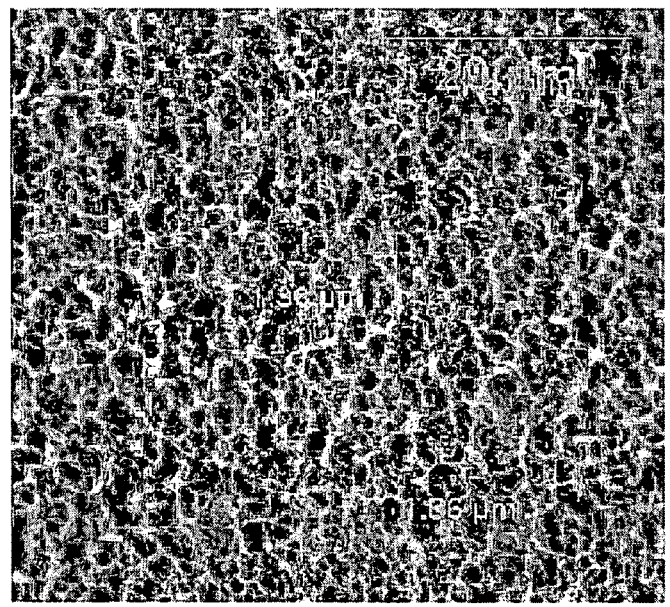
Figure 5D:
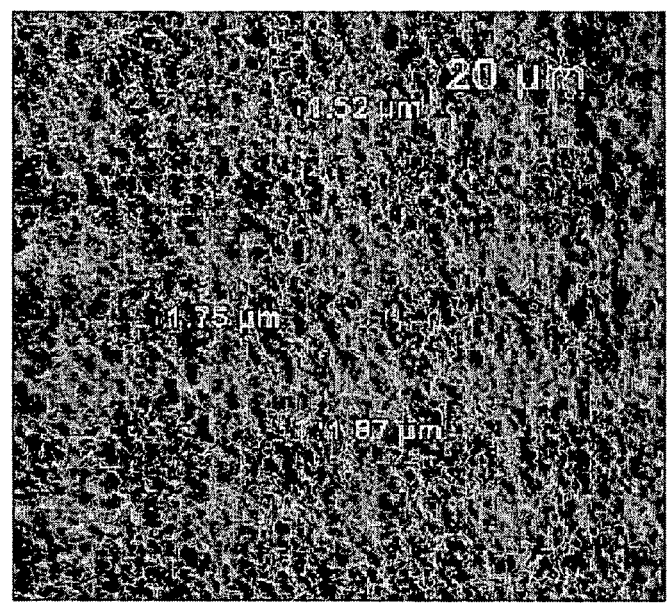

FIGS. 4 A and B report the surfaces produced when the native oxide was removed by the usual method and then the surface was etched with an HCl solution. Although some pitting occurred, it was evident that HCl alone was not sufficient to produce a surface like that of FIG. 1C.

FIGS. 5 A-D illustrate the improved results that were obtained when small amounts of HF were added to the 20 wt % HCl etching solution. It was concluded that a small amount of HF should be used if the desired surface topography was to be obtained. The surfaces of FIGS. 5C and 5D were given the same treatment and produced substantially the same surface, even though the C and D samples had different machining and heats. Thus, it was concluded that the process was broadly applicable to Ti 6/4 alloys.

In the presently preferred process, Ti 6/4 alloy is immersed in an aqueous solution of hydrofluoric acid for the length of time required to remove the native oxide while not removing a significant amount of metal. A preferred solution, suitable for commercial application would contain about 7.9 to 9.0 wt % HF. However, more or less concentrated solutions could be used, with appropriate adjustment of the exposure time, provided that the native oxide was removed to prepare the surface for subsequent etching needed to create the desired surface topography.

The etching step immerses the Ti 6/4 alloy, from which the native oxide had been removed, in an aqueous solution at room temperature containing about 0.053 to 0.105 wt % HF and 19-21 wt % HCl. Such solutions have been found to produce the desired surface topography on Ti 6/4 alloy within about 20 minutes and using only ambient temperatures. Again, some adjustment of the acid concentrations, temperature, and exposure time is believed to be possible, while still obtaining the desired surface. It is believed that equivalent results may be obtained within the broader range of 0.005 to 1.0 wt % HF and 10-30 wt % HCl.

Dental Implants

Figure 6:
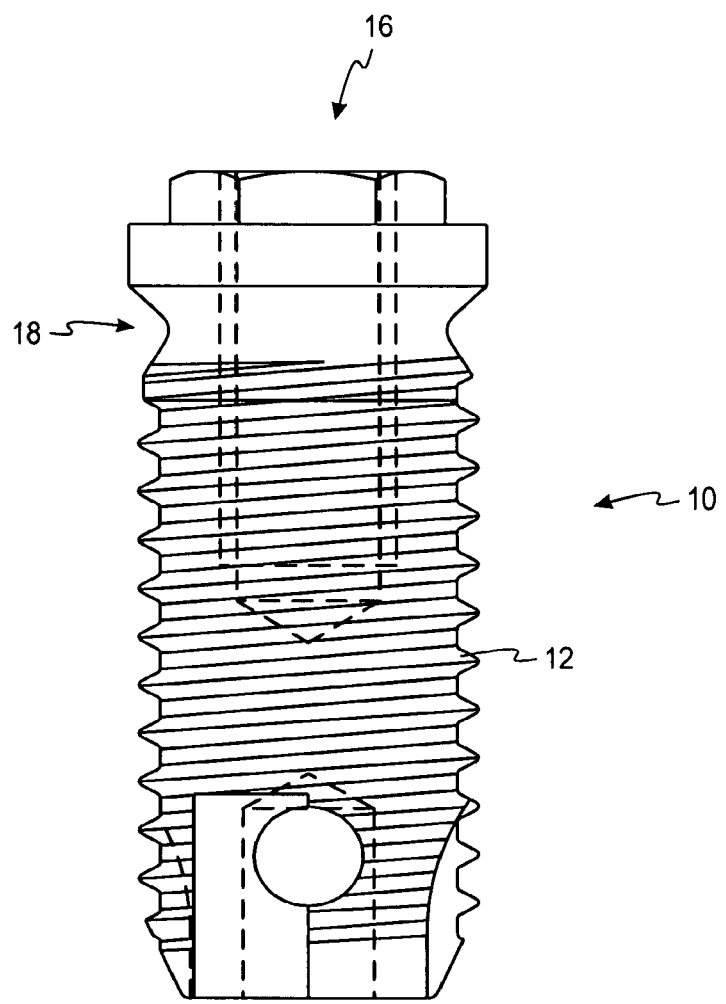
FIG. 6 shows a typical dental implant.

The etching process of the invention may be used to prepare the surface of various styles of dental implants. A typical example is illustrated in FIG. 6. The implant 10 will be placed in a pre-drilled hole in a patient's bone to replace the root of a missing tooth. The threaded portion 12 engages the bone, while at least some of the upper portion 14 contacts tissue. In many cases, the etching process will be applied to the threaded portion 12 of the implant 10, while the upper portion 14, shown in FIG. 6 to include a head 16 portion for engaging dental prothesis components and a neck portion 18, remains relatively smooth. In some cases, the roughened area may be extended upward into the neck and head regions, or even to the top of the implant 10. In other cases, only a portion of the threads will be roughened to improve osseointegration of the metal with bone, while the upper section of the threaded region will remain relatively smooth.

What is claimed is:

1. A method of producing a uniformly roughened surface on Ti 6/4 alloy for contact with living bone comprising:
    treating least a portion of the implant surface for a suitable period of time to create a first surface; and
    contacting the first surface with a first aqueous solution including hydrofluoric acid and hydrochloric acid for a suitable period of time to create a second surface having a topography for osseointegration of the implant with living bone, the topography having irregularities with peak-to-valley heights of less than 10 microns, wherein the first aqueous solution includes about 0.005 to about 1.0 wt% hydrofluoric acid and about 10 to about 30 wt% hydrochloric acid.

2. The method of claim 1 further comprising removing native oxide from the Ti 6/4 alloy prior to treating by contacting the alloy with a second aqueous solution for a suitable period of time, the second aqueous solution including hydrofluoric acid.

3. The method of claim 2 wherein the second aqueous solution contains about 7.9 to about 9.0 wt% hydrofluoric acid.

4. The method of claim 1 further comprising:
    rinsing the first surface after the treating to remove residual debris; and
    rinsing the second surface after the contacting the first surface with the first aqueous solution to remove residual first aqueous solution.

5. The method of claim 1 wherein the first aqueous solution includes about 0.0845 wt% hydrofluoric acid and about 20 wt% hydrochloric acid.

6. A method of producing a uniformly roughened surface on a Ti 6/4 alloy implant for contact with living bone, the implant having a head section, a neck section below the head section, and a threaded section below the neck section, the method comprising:
    treating at least a portion of the neck section and at least a portion of the threaded section directly below the neck section for a suitable period of time to create a first surface;
    contacting the first surface with a first aqueous solution including hydrofluoric acid and hydrochloric acid for a suitable period of time to create a second surface having a topography for osseointegration of the implant with living bone, the topography having peak-to-valley heights of less than 10 microns, wherein the first aqueous solution includes about 0.005 to about 1.0 wt% hydrofluoric acid and about 10 to about 30 wt% hydrochloric acid.

7. The method of claim 6 further comprising removing native oxide from the neck section and the threaded section prior to the act of treating by contacting the alloy with a second aqueous solution for a suitable period of time, the second aqueous solution including hydrofluoric acid.

8. The method of claim 7 wherein the second aqueous solution contains about 7.9 to about 9.0 wt% hydrofluoric acid.

9. The method of claim 6 further comprising:
    rinsing the first surface after the treating to remove residual debris; and
    rinsing the second surface after the contacting the first surface with the first aqueous solution to remove residual first aqueous solution.

10. The method of claim 6 wherein the first aqueous solution includes about 0.0845 wt% hydrofluoric acid and about 20 wt% hydrochloric acid.

11. A method of producing a uniformly roughened surface on Ti 6/4alloy for contact with living bone comprising:
    treating least a portion of the implant surface with an aqueous solution for a suitable period of time to remove native oxide from the implant surface to create a first surface; and
    contacting the first surface with a first aqueous solution including hydrofluoric acid and hydrochloric acid for about twenty (20) minutes at ambient temperature to create a second surface having a topography for osseointegration of the implant with living bone, the topography having peak-to-valley heights of less than 10 microns, wherein the first aqueous solution includes about 0.005 to about 1.0 wt% hydrofluoric acid and about 10 to about 30 wt% hydrochloric acid.

* * * * *